(12) United States Patent
Stefanchik

(10) Patent No.: US 7,780,691 B2
(45) Date of Patent: Aug. 24, 2010

(54) ENDOSCOPIC TISSUE RESECTION DEVICE

(75) Inventor: David Stefanchik, Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 533 days.

(21) Appl. No.: 11/689,125

(22) Filed: Mar. 21, 2007

(65) Prior Publication Data

US 2008/0234693 A1    Sep. 25, 2008

(51) Int. Cl.
*A61B 17/32* (2006.01)
*A61B 1/00* (2006.01)

(52) U.S. Cl. ...................................... 606/170; 600/106

(58) Field of Classification Search .................. 600/101, 600/104, 106, 121, 123, 137, 149; 606/170–171, 606/45–47; 74/20–25; 604/95.01, 528
See application file for complete search history.

(56) References Cited

U.S. PATENT DOCUMENTS

| | | | |
|---|---|---|---|
| 3,595,239 A | | 7/1971 | Petersen |
| 4,137,920 A | * | 2/1979 | Bonnet ........................ 606/171 |
| 4,770,653 A | * | 9/1988 | Shturman ...................... 606/7 |
| 5,075,062 A | | 12/1991 | Karpiel |
| 5,364,393 A | | 11/1994 | Auth et al. |
| 5,613,950 A | | 3/1997 | Yoon |
| 5,810,807 A | | 9/1998 | Ganz et al. |
| 6,554,845 B1 | | 4/2003 | Fleenor et al. |
| 6,561,998 B1 | | 5/2003 | Roth et al. |
| 6,743,240 B2 | | 6/2004 | Smith et al. |
| 6,997,931 B2 | | 2/2006 | Sauer et al. |
| 7,048,733 B2 | | 5/2006 | Hartley et al. |
| 7,052,492 B2 | | 5/2006 | Swanson et al. |
| 2005/0033285 A1 | | 2/2005 | Swanson et al. |
| 2005/0197623 A1 | | 9/2005 | Leeflang et al. |

(Continued)

FOREIGN PATENT DOCUMENTS

EP    0465449    1/1992

(Continued)

OTHER PUBLICATIONS

U.S. Appl. No. 11/380,952, filed May 1, 2006, Stefanchik et al.

(Continued)

*Primary Examiner*—Gary Jackson
*Assistant Examiner*—Ashley Cronin

(57) ABSTRACT

Devices and methods useful for manipulating tools at a surgical site are disclosed. The disclosed devices and methods can be useful, for example, for orbiting the distal end of one tool around the distal end of another tool, such as in an endoscopic resection procedure, and/or for rotating a tool or an end effector. In one exemplary embodiment, an endoscopic device is provided and can include an elongate shaft having a first lumen and a second lumen formed therein, each of the first and the second lumens adapted to receive a tool therethrough. A rotatable element can be disposed at a distal end of the elongate shaft, the rotatable element having a lumen formed therein that is associated with the first lumen of the elongate shaft and also having a tool guide that is adapted to receive a tool and that is associated with the second lumen of the elongate shaft. The rotatable element can be configured to rotate on a longitudinal axis thereof such that the tool guide orbits the longitudinal axis of the rotatable element.

11 Claims, 8 Drawing Sheets

U.S. PATENT DOCUMENTS

| | | |
|---|---|---|
| 2005/0228286 A1 | 10/2005 | Messerly et al. |
| 2005/0234297 A1 | 10/2005 | Devierre et al. |
| 2005/0277954 A1 | 12/2005 | Smith et al. |
| 2006/0048787 A1* | 3/2006 | Manzo ................ 128/898 |
| 2006/0079889 A1 | 4/2006 | Scott |
| 2008/0188869 A1* | 8/2008 | Weitzner et al. ............ 606/130 |

FOREIGN PATENT DOCUMENTS

| | | |
|---|---|---|
| WO | WO2004054878 | 1/2004 |
| WO | WO2005081202 | 1/2005 |

OTHER PUBLICATIONS

U.S. Appl. No. 11/381,016, filed May 1, 2006, Blakos.

U.S. Appl. No. 11/425,525, filed Jun. 21, 2006, Messerly et al.

* cited by examiner

ENDOSCOPIC TISSUE RESECTION DEVICE

FIELD OF THE INVENTION

The present invention generally relates to methods and devices for manipulating tools at a surgical site.

BACKGROUND OF THE INVENTION

Endoscopic surgical methods and devices are often preferred over traditional open surgical methods and devices because the use of a natural orifice tends to reduce postoperative recovery time and complications. Consequently, significant development has gone into a range of endoscopic surgical devices that are suitable for precise placement of a working end of a tool at a desired surgical site through a natural orifice. These tools can be used to engage and/or treat tissue in a number of ways to achieve a diagnostic or therapeutic effect.

The ability to manipulate a tool at a surgical site can be limited. For example, the devices and methods used to place a tool endoscopically can restrict its movement relative to the surgical site, to the endoscope, or to other tools. Many endoscopic procedures require that surgical tools be manipulated in ways difficult to achieve due to these restrictions. For example, oftentimes it is desirable that the working end of a tool be rotated, or moreover that the tool be rotated with a reasonably precise degree of control. Such rotation may be hard or impossible due to the shape, size and capabilities of the endoscopic device used and/or the lack of suitable controls for remotely effecting suitable movement. In other cases, it may be desirable to revolve or orbit the working end of one tool around that of another tool. For example, in a resection procedure it may be desired to revolve a cutting tool around tissue held by a grasping tool to create a circular incision. These procedures, and others, would benefit from improved devices and methods for effecting such movement of tools at a surgical site, and from devices and methods for effecting such movement remote from the surgical site or from a proximal end of the tools or endoscope placed at the surgical site.

Accordingly, there is a need for improved devices and methods for manipulating tools at a surgical site.

SUMMARY OF THE INVENTION

In one embodiment, an endoscopic device is provided having an elongate shaft and a rotatable element. The elongate shaft can have a first lumen and a second lumen formed therein, each lumen being adapted to receive a tool therethrough. In some embodiments, the elongate shaft can be adapted to be inserted through the working channel of an endoscope. The rotatable element can be disposed at a distal end of the elongate shaft and can have a lumen formed therein that is associated with the first lumen of the elongate shaft. The rotatable element can also have a tool guide that is adapted to receive a tool and that is associated with the second lumen of the elongate shaft. The rotatable element can be configured to rotate on a longitudinal axis thereof so that the tool guide orbits that longitudinal axis of the rotatable element.

The rotatable element can have a variety of other configurations. The rotatable element can be placed or arranged at least partially within the first lumen of the elongate shaft. In some embodiments, the rotatable element can include a spool for receiving a control wire, and rotation of the spool causes the rotatable element to rotate on the longitudinal axis thereof. In other embodiments, the rotatable element can include an engagement surface for engaging a control wire that is configured to rotate the rotatable element on the longitudinal axis thereof. In yet other embodiments, the tool guide of the rotatable element can be formed on its exterior surface.

The endoscopic device can have a wide variety of further features. For example, in some embodiments the endoscopic device can include a control wire that is disposed through a control wire lumen formed in the elongate shaft. Movement of the control wire can cause the rotatable element to rotate on the longitudinal axis thereof. In other embodiments, the endoscopic device can include a control wire that extends through first and second control wire lumens formed in the elongate shaft and that is wrapped at least partway around a spool formed on the rotatable element. The endoscopic device can also include a control spool associated with a proximal end of the elongate shaft with the control wire wrapped at least partway thereon, and movement of the control spool can cause the rotatable element to rotate on the longitudinal axis thereof. In yet other embodiments, the endoscopic device can include a cutting tool that is adapted to be removeably and replaceably extended through the second lumen of the elongate shaft and received by the tool guide. Rotation of the rotatable element on the longitudinal axis can orbit the distal end of the cutting tool around the longitudinal axis of the rotatable element.

An endoscopic system is also provided herein, which in one embodiment can have an elongate shaft, an end effector, and a rotation mechanism. The elongate shaft can have proximal and distal ends and a lumen formed therein for receiving a tool therethrough. The end effector can be disposed at a distal end of the elongate shaft and can have a spool formed on it. The rotation mechanism can be coupled to the spool and configured to rotate the end effector on the longitudinal axis of the end effector.

A variety of further configurations are possible. For example, the end effector can be disposed at least partially within the lumen of the elongate shaft. The end effector can have a lumen formed therein that is contiguous with the lumen of the elongate shaft. The end effector can also include a tool guide that is adapted to receive a tool and that is formed on an exterior surface of the end effector, such that rotation of the end effector can cause the tool guide to orbit around the longitudinal axis of the end effector. In some embodiments, the rotation mechanism can include a control wire that extends through each of two control wire lumens that are formed in the elongate shaft, and the control wire can also be disposed at least partway around the spool. In other embodiments, the rotation mechanism can further include a control spool that is associated with a proximal end of the elongate shaft with the control wire wrapped at least partway thereon. Movement of the control spool can be effective to rotate the end effector on the longitudinal axis thereof. In yet other embodiments, the system can include an endoscope having a working channel associated with it, and the elongate shaft can be adapted to extend through the working channel.

In other aspects, a method for manipulating a tool is provided. In one embodiment, an exemplary method includes advancing an endoscopic device through a working channel associated with an endoscope, the endoscopic device having an elongate shaft with a rotatable element disposed at its distal end. The method can further include inserting a tool through a lumen formed in the elongate shaft and a lumen formed in the rotatable element, and also can include rotating the rotatable element. The rotation of the rotatable element can include moving a control wire on spool formed on the rotatable element.

A variety of further techniques can be used. In some embodiments, a second tool can be inserted through a second lumen formed in the elongate shaft, and rotation of the rotatable element can include orbiting a distal end of the second tool around a distal end of the first tool. Virtually any surgical tool can be used, including cutting tools, grasping tools, snare loop tools, and so on. In other embodiments, a second tool can be inserted through a second lumen formed in the elongate shaft and a distal end of a second tool can be coupled to a tool guide disposed on an exterior surface the rotatable element. The rotation of the rotatable element can include orbiting a distal end of the second tool around a distal end of the first tool. In yet other embodiments, after advancing the endoscopic device, the second tool can be axially slid through an opening formed in the tool guide to adjust a position of a distal end of the second tool relative to a distal end of the endoscopic device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices useful for manipulating tools at a surgical site. In some cases access to the surgical site can be gained translu-menally, e.g., through a body lumen and/or a natural orifice of the body. The devices and methods are particularly useful for manipulating tools at the working end of a viewing instrument such as an endoscope, for example as part of an endoscopic resection procedure. Although some of the embodiments disclosed herein will be described in the context of an endoscopic resection procedure, they are not limited to such applications. The devices and methods described herein may be used with a wide variety of viewing instruments and/or other tools, including tools unrelated to tissue resection or tissue-cutting. Moreover, they may be used in a wide range of other procedures including non-endoscopic procedures, such as laparoscopic and open surgical procedures, and in virtually any medical procedure now or later in use.

Figure 1:
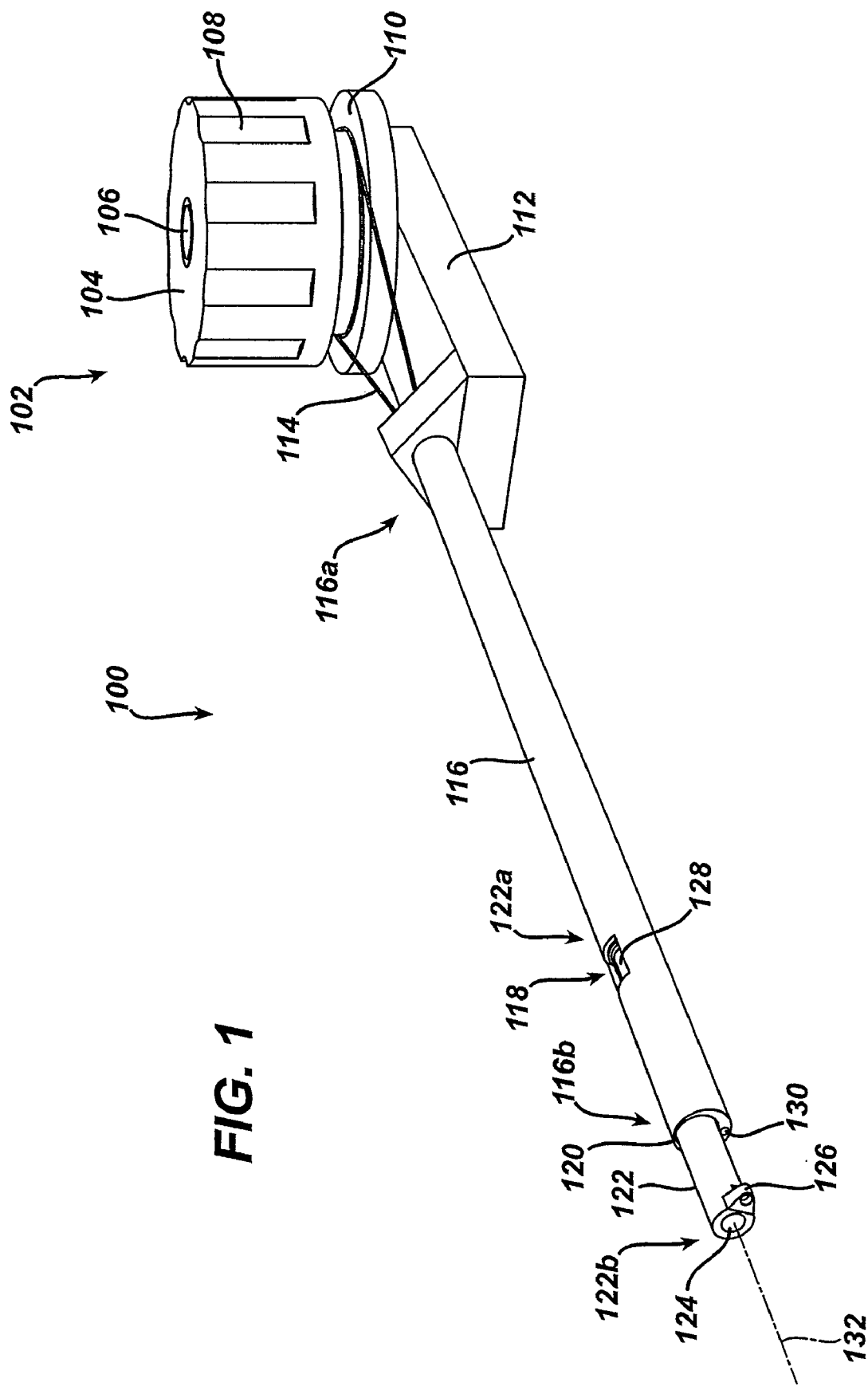
FIG. 1 is a perspective view of one exemplary embodiment of an endoscopic device having an elongate shaft with a rotatable element at a distal end thereof and a control assembly at a proximal end thereof.
Figure 2:
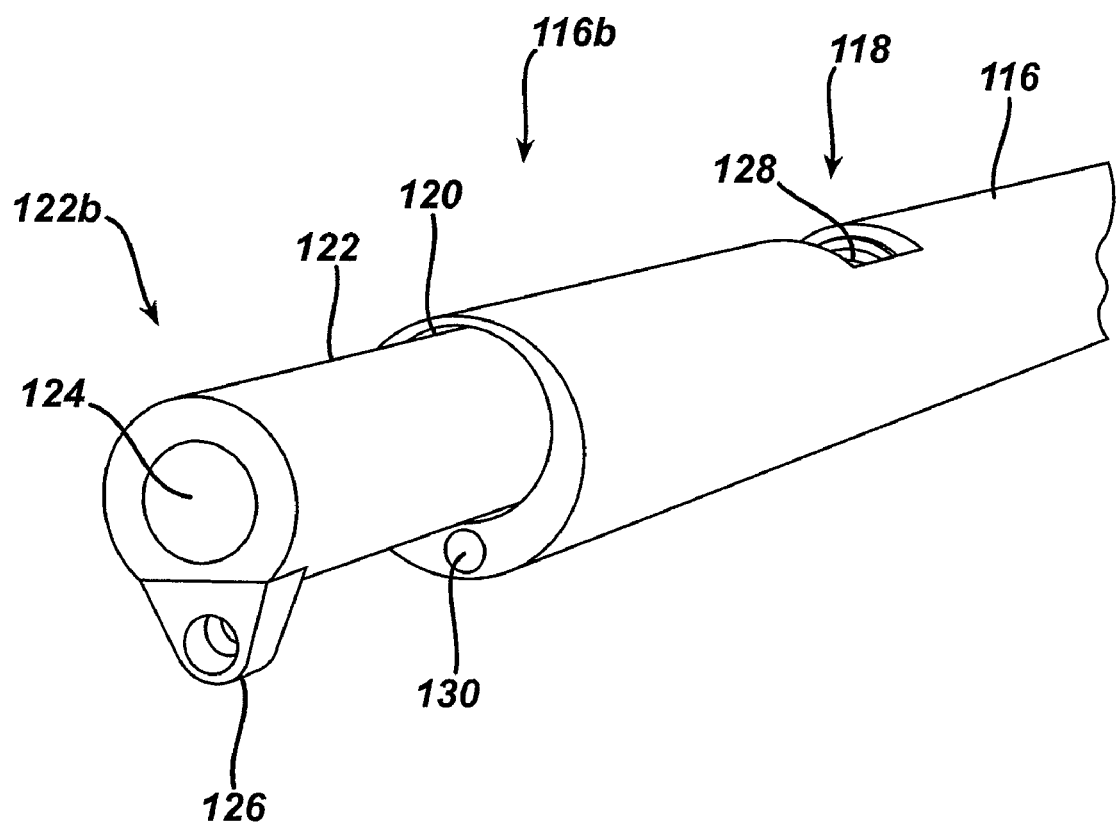
FIG. 2 is an enlarged view of a distal portion of the endoscopic device shown in FIG. 1.
Figure 3:
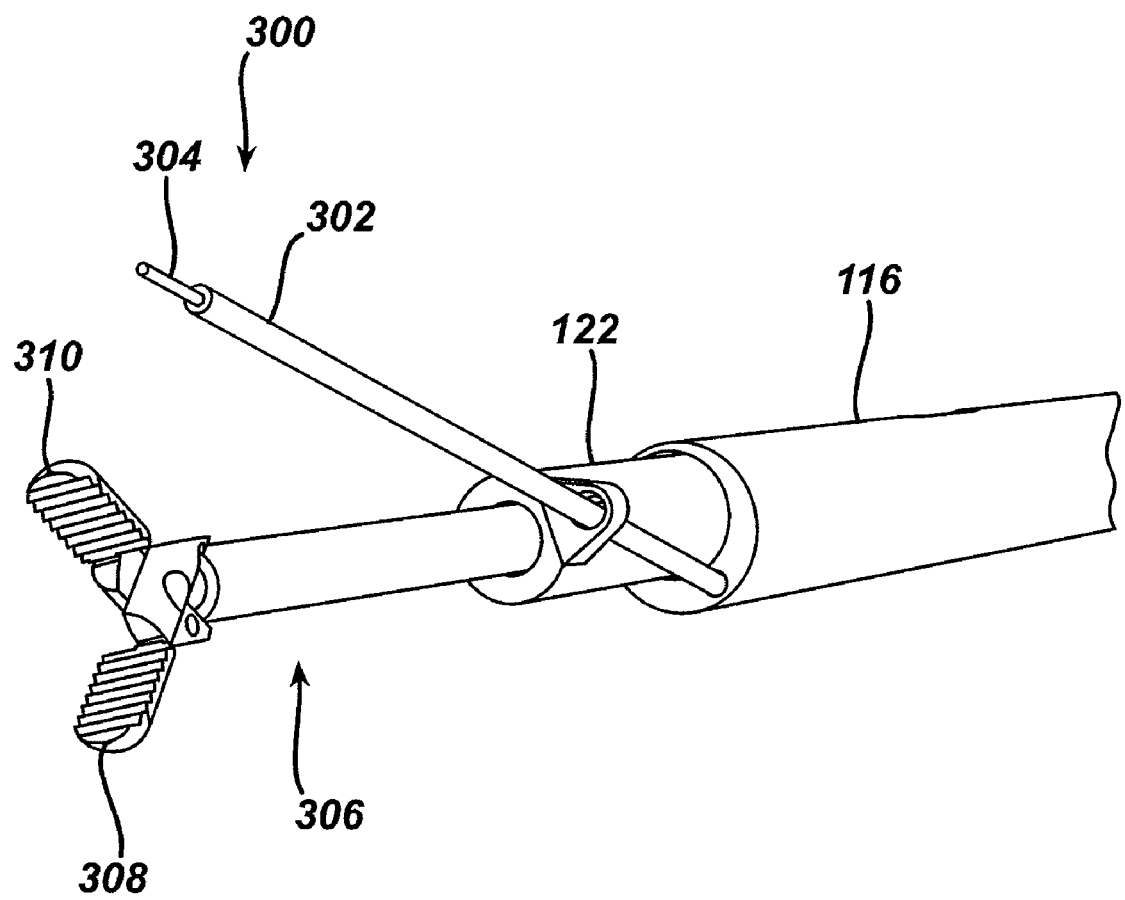
FIG. 3 is an enlarged view of a distal portion of the endoscopic device shown in FIG. 1 with two exemplary tools extending therethrough.

FIGS. 1-2 illustrate one exemplary embodiment of an endoscopic device 100. The endoscopic device 100 can have a variety of configurations, but as shown in the illustrated embodiment the endoscopic device 100 can include an elongate shaft 116 and an end effector such as a rotatable element 122 disposed at a distal end 116b thereof. The elongate shaft 116 can have a first lumen 120 and a second lumen 130 formed therein between proximal and distal ends 116a, 116b thereof. Each of these lumens 120, 130 can be adapted to receive a tool therethrough. The rotatable element 122 can be disposed at the distal end 116b of the elongate shaft 116 and a proximal portion of the rotatable element 122 can extend into the lumen 120 of the elongate shaft while a distal portion of the rotatable element 122 extends beyond the distal end 116b of the elongate shaft 116. The rotatable element 122 can have a lumen 124 formed therein, and the lumen 124 can be connected to the lumen 120 of the elongate shaft 116 such that a tool or other object can extend through both lumens 120 and 124. The rotatable element 122 can also have a tool guide 126 formed thereon and adapted for receiving a tool. In addition, the rotatable element 122 can be configured to axially rotate within the lumen 120 of the elongate shaft 116 such that the tool guide 126 orbits a longitudinal axis, such as axis 132, of the rotatable element 122. The rotatable element 124 can have an engagement surface in the form of a spool 128, which is shown through the window 118 in the elongate shaft 116. (The window 118 is not necessary and is included herein to provide a better understanding of the endoscopic device 100 by illustrating the spool 128.) A control wire 114 can be wrapped at least partway around this spool 128 such that movement of the control wire 114 can cause the spool 128 to rotate around a longitudinal axis thereof. The elongate shaft 116 can have first and second control wire lumens 500, 502 (shown in more detail in FIG. 5 and discussed below) formed therein for receiving the control wire 114. The control wire lumens 500, 502 can extend from the spool 128 to a proximal end 116a of the elongate shaft 116, allowing the control wire 114 therein to extend from the spool 128 to the control assembly 102 disposed at the proximal end 116a of the elongate shaft 116. As shown, the control assembly 102 can include a handle 112 and a control such as a knob 104. The knob 104 can be coupled to a control spool 110. The control wire 114 can be wrapped at least partway around the control spool 110. In use, turning the knob 104 can move the control wire 114 disposed on the spool 128 and cause the rotatable element 122 to rotate. Rotation of the rotatable element 122 can be effective to cause the tool guide 126 to orbit or revolve around a longitudinal axis, such as axis 132 extending through lumen 124, of the rotatable element 122. As will be discussed in more detail below, in some applications a distal end of a tool that extends through the second lumen 130 of the elongate shaft 116 and that is received by the tool guide 126 can orbit around a distal end of a tool extending through the first lumen 120 of the elongate shaft 116 and through the lumen 124 of the rotatable element 122. FIG. 3 shows exemplary tools, such as a needle-knife 300 and a grasper 306, that can be used with the endoscopic device 100.

Figure 4:
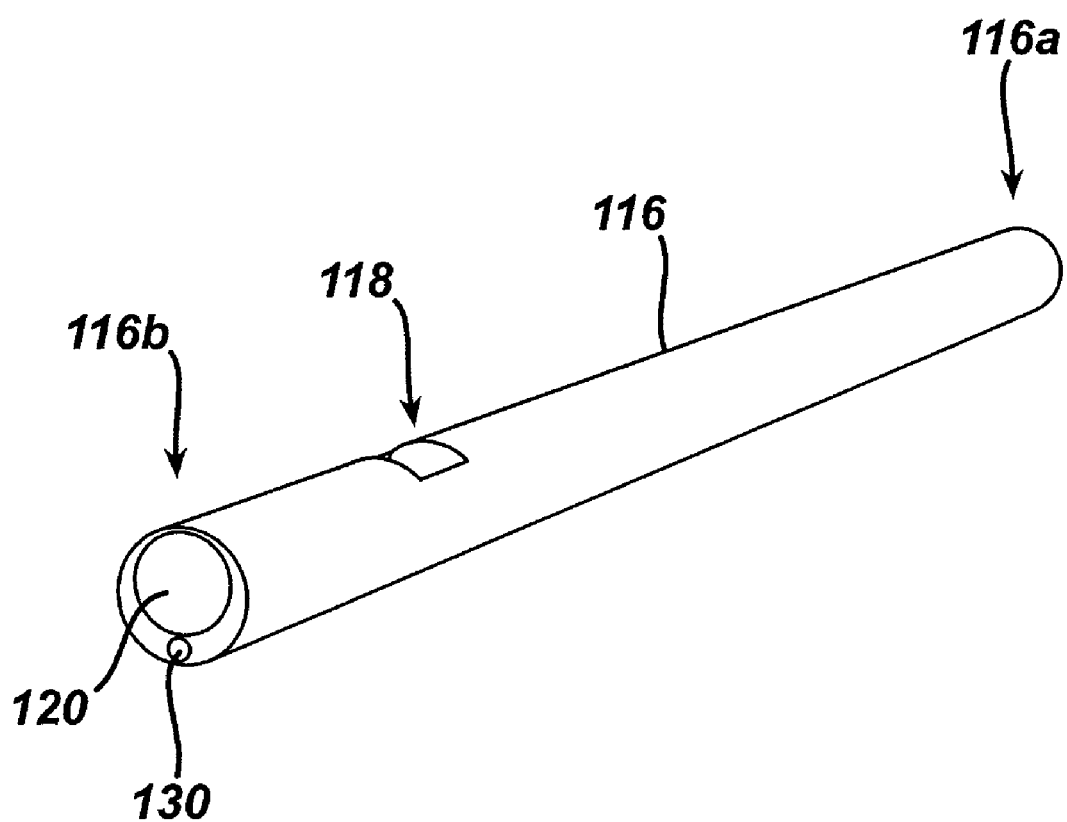
FIG. 4 is a perspective view of the elongate shaft shown in FIG. 1.
Figure 5:
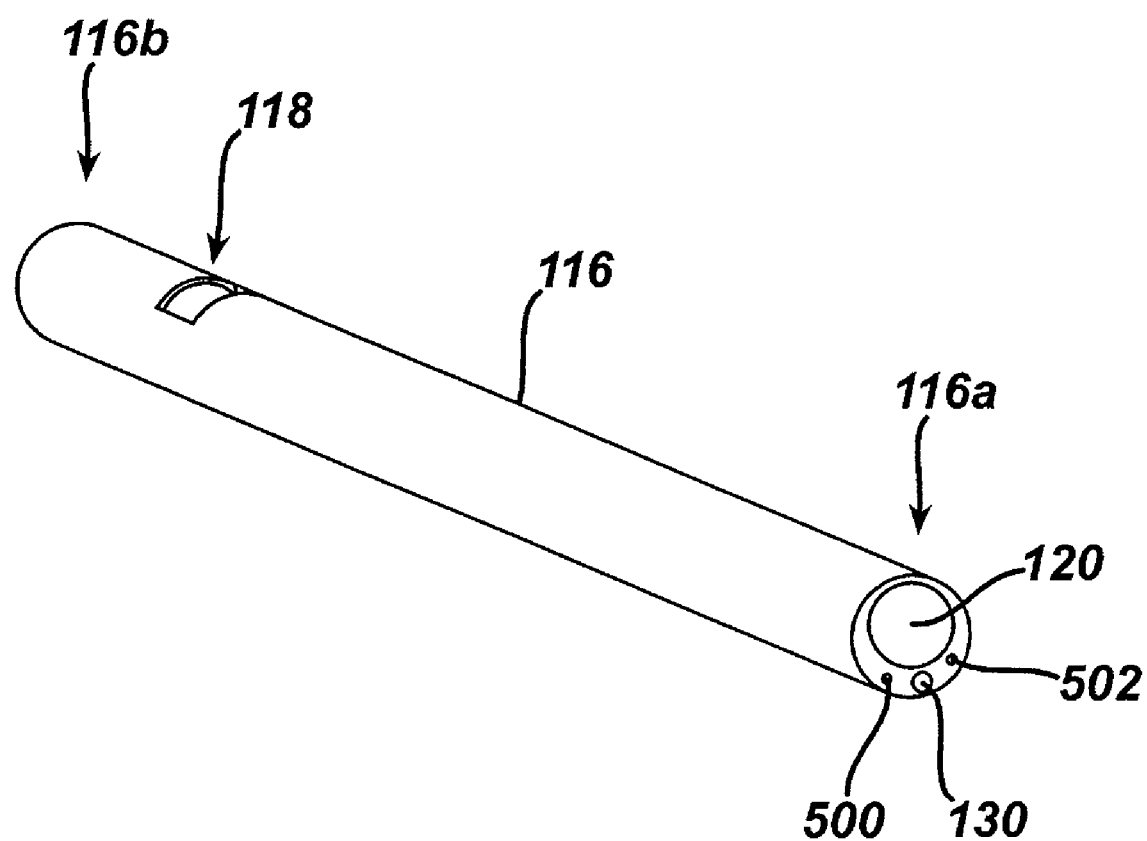
FIG. 5 is a view of the elongate shaft shown in FIG. 4 from an perspective opposite that of FIG. 4 and illustrating a proximal end of the elongate shaft.
Figure 6:
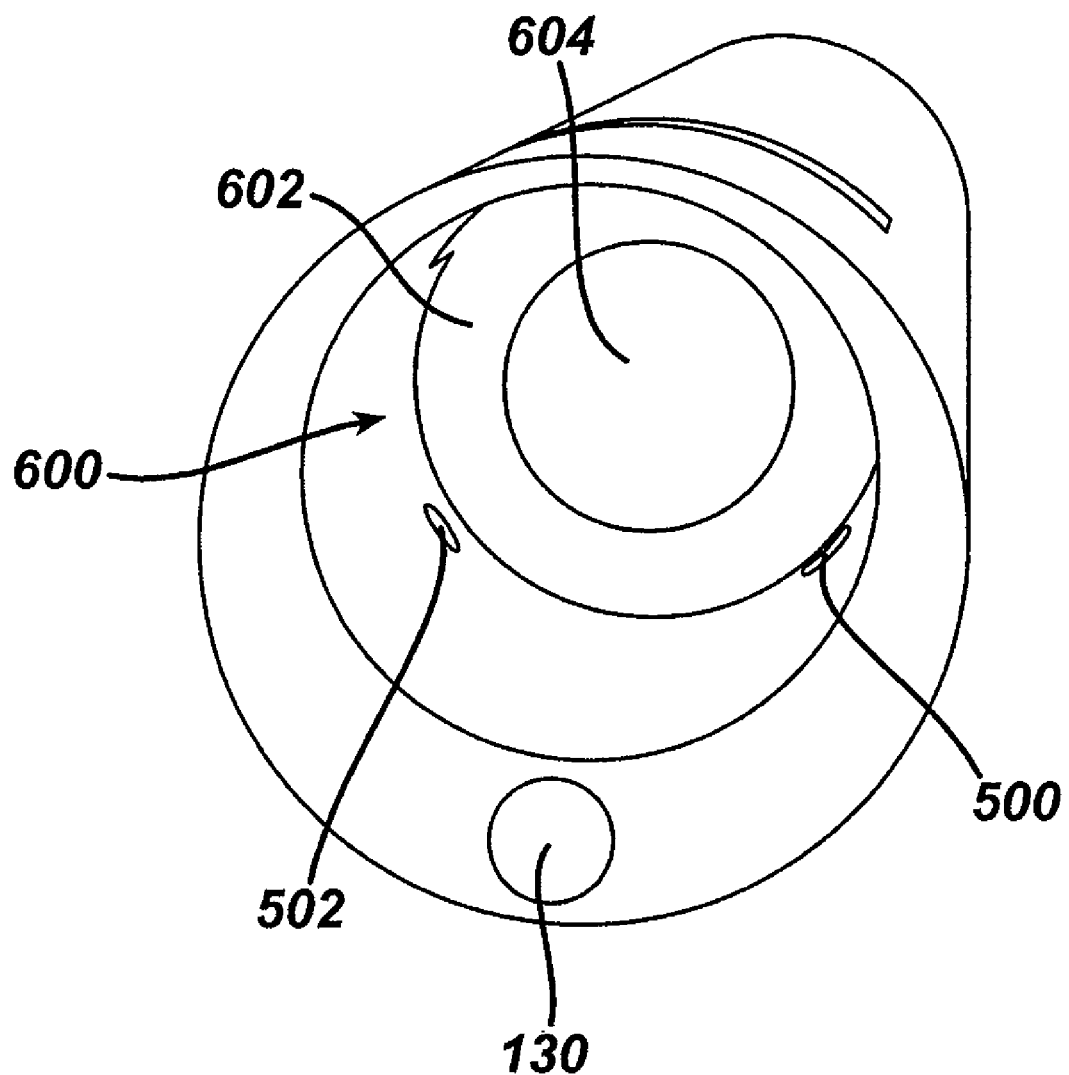
FIG. 6 is an enlarged view of a distal portion of the elongate shaft shown FIG. 4.

The elongate shaft 116 can have a variety of configurations, but as shown in the illustrated embodiment of FIGS. 4-6, the elongate shaft 116 is a tube that has a proximal end 116a adapted to remain outside the body and a distal end 116b adapted to be positioned within the body at or near a surgical site. The elongate shaft 116 can be a rod, sheath, or virtually any other form. The elongate shaft 116 can also be of virtually any length or size, although in some embodiments the elongate shaft 116 can be sized or otherwise adapted to be received through a working channel associated with an endoscope. The elongate shaft 116 can be adapted to slide axially within such a working channel, for example, to translate relative to the endoscope, and can have surface features formed on an exterior surface thereof to create selectable positions and/or allow for controllable positioning of the elongate shaft 116 as it moves within the working channel of the endoscope. The surface features, for example, can include indentations, ridges, notches, or grooves formed on the elongate shaft 116 and can complement features formed in the working channel. In other embodiments, the elongate shaft 116 can be sized or otherwise adapted to be inserted into the body, translumenally for example, separate from or without any endoscope. Any cross-sectional shape is possible for the elongate shaft 116, including circles, rectangles, squares, ovals, ellipses, and so on. In addition, the elongate shaft 116 or portions thereof can be flexible. The elongate shaft 116 can be made of a flexible material or can include articulating segments placed in desired locations to provide a desired degree of suppleness. A flexible elongate shaft 116 can be advantageous in some applications, for example, where it is desired to advance the elongate shaft 116 through a tortuous body lumen, or where the elongate shaft 116 extends through a flexible working channel associated with an endoscope and the working channel is advanced through a tortuous body lumen. A flexible elongate shaft 116 can also accommodate articulation or steering of a tool disposed therethrough, such as an endoscope with an articulating distal end.

As shown in FIGS. 4-6, the elongate shaft 116 can have a first lumen 120 and a second lumen 130 formed therein and adapted for receiving a tool therethrough. While illustrated as circular, the interior of the lumens 120, 130 can be of any size and shape suitable to receive a tool. The lumens 120, 130 can be adapted to allow a tool to slide axially while disposed therein, or can be adapted to hold the tool, e.g., via a frictional fitting, interference fit, or a fastener. The lumens 120, 130 can have surface features formed therein, such as indentations, ridges, and so on, as part of such adaptations. As shown, the lumens 120, 130 extend from a proximal end 116a to a distal end 116b of the elongate shaft. One or more of the lumens 120, 130 can also extend partway along the elongate shaft 116, e.g., from the distal end 116b to a lateral opening formed on the surface of the elongate shaft 116. The first lumen 120 can include an enlarged part or mouth 600 extending between an interior wall 602 and the distal end 116b of the elongate shaft 116. The first lumen 120 can be seen in FIG. 6 to continue proximally from the interior wall 602 through a constricted portion 604 having a diameter smaller than the diameter of the mouth 600. The mouth 600 can be adapted to receive the rotatable element 122, as previously mentioned, and to allow the rotatable element 122 to rotate therein. In some embodiments, the first lumen 120 can be omitted entirely, and a bore, notch, cylindrical recess, or cutout, which may resemble the lumen 120 without the constricted portion 604, can be formed in the distal end 116b of the elongate shaft 116 to receive the rotatable element 122. As previously mentioned, the elongate shaft 116 can also have control wire lumens 500, 502 extending therethrough. The control wire lumens 500, 502 can have a wide variety of configurations, but in the illustrated embodiment the control wire lumens 500, 502 extend from a proximal end 116a of the elongate shaft 116 (shown in FIG. 5) to an interior surface of the mouth 600 of the first lumen 120 (shown in FIG. 6). The control wire lumens 500, 502 can open into the mouth 600 so as to provide access to the rotatable element 122 and/or the spool 128 of the rotatable element 122.

As one skilled in the art will appreciate, FIGS. 1-6 show the elongate shaft 116 with a window 118 formed therein for purposes of illustration and explanation of the spool 128. In some embodiments, the window 118 can be advantageous for providing access to the spool 128 or other aspects of the rotatable element 122. However, a window 118 is not necessary and preferably is omitted from the elongate shaft 116.

Figure 7:
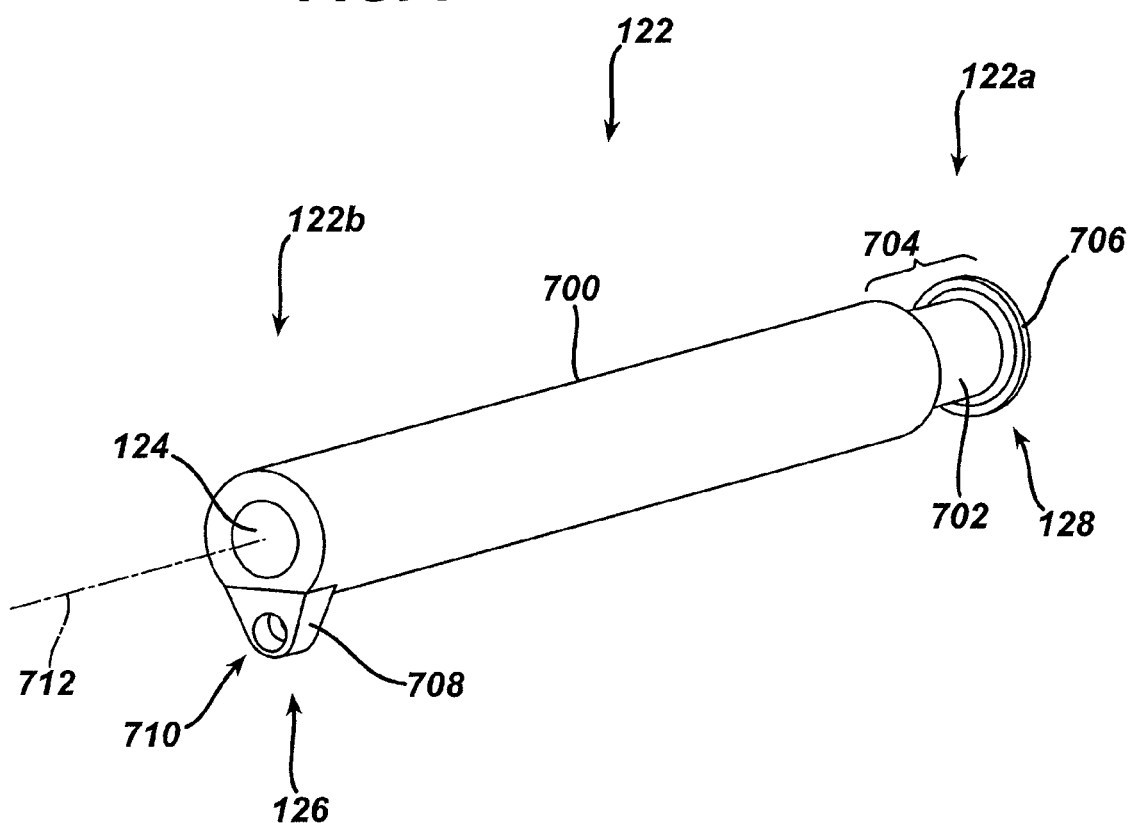
FIG. 7 is a perspective view of the rotatable element shown in FIG. 1.

The rotatable element 122 can have a wide variety of configurations, but as shown in FIG. 7, the rotatable element 122 is in the form of a shaft 700 with a lumen 124 formed therein and an engagement surface in the form of a spool 128 disposed at a proximal end 122a thereof. The rotatable element 122 can also be in the form of a ring, bushing, plug, and so on, that is movably coupled to the distal end of elongate shaft 116. Although the rotatable element 122 can have virtually any length, the rotatable element 122 advantageously can be sized such that a portion of the rotatable element can be disposed within the mouth 600 of the elongate shaft 116. Alternatively, the rotatable element 122 can be adapted to be disposed entirely within the elongate shaft 116. The rotatable element 122 can be configured to rotate on a longitudinal axis 712 thereof. For example, the rotatable element 122 can be sized so as to be capable of rotating when disposed within the lumen 120 of the elongate shaft 116, e.g., the rotatable element can be sufficiently loose to allow for movement, or can have bushings or ball bearings disposed on the shaft 700 to facilitate rotation. Although shown as substantially smooth in FIG. 7, the shaft 700 can also have virtually any kind of surface features formed thereon, such as indentations, rims, or notches. Complementary surface features can be formed in the lumen 120 of the elongate shaft 116. Such surface features can be advantageous for controlling or preventing movement, e.g., rotation and/or longitudinal movement along axis 712, of the rotatable element 122 when disposed within the lumen 120 of the elongate shaft 116. For example, longitudinal ridges formed on the shaft 700 can define selectable rotational positions for the rotatable element 122. As another example, an annular ridge formed on the shaft 700, along with a complementary annular groove formed in lumen 120, can be effective to prevent or inhibit longitudinal movement of the rotatable element 122 along axis 712.

As previously mentioned, the rotatable element 122 can have a lumen 124 adapted to receive a tool therethrough. The lumen 124 optionally can have a diameter or width substantially similar to that to the of constricted portion 604 of the lumen 120 in the elongate shaft 116. As a result, the constricted portion 604 of the elongate shaft 116 and the lumen 124 of the rotatable element 122 can form a substantially contiguous lumen when the rotatable element 122 is disposed against or abuts the wall 602 of the elongate shaft 116. Such an arrangement can advantageously provide a pathway for a tool from the proximal end 116a of the elongate shaft 116 to the distal end 122b of the rotatable element 122. The rotatable element 122 can also have any numbers of additional lumens formed therein, for example to accommodate additional tools extending therethrough.

The rotatable element 122 can have an engagement surface formed thereon and the engagement surface can have a wide variety of configurations. As previously mentioned, in the illustrated embodiment shown in FIG. 1 and in more detail in FIG. 7, the engagement surface is in the form of a spool 128. As shown, the spool 128 is in the form of a recessed surface 702 on the shaft 700 with a flange 706 disposed at a proximal end 122a thereof. The recessed surface 702 can have virtually any length 704 and can be located at virtually any point on the shaft 700. The recessed surface 702 can be adapted to receive a control wire 114, for example, a control wire 114 can be wrapped at least partway thereon and/or attached to thereto. The recessed surface 702 can have friction-enhancing surface features for facilitating the grip of the control wire 114 thereon or control wire guides such as screw-like ridges for guiding the wrapping of the control wire 114 thereon. The spool 128 can have teeth formed thereon, e.g., for engaging gears or a chain, ridges, tabs or virtually any other feature suitable for effecting movement of the rotatable element 122. The engagement surface 702 can also have one or magnetic or electromagnetic elements, such as permanent magnets or wire coils for effecting movement of the rotatable element 122 in cooperation with complementary magnetic or electromagnetic elements disposed in the lumen 120 of the elongate shaft 116, e.g., as a controllable electric motor.

The rotatable element 122 can also have a tool guide 126 formed thereon for receiving a tool. The tool guide 126 can have a variety of configurations, but in FIG. 7 the tool guide 126 is in the form of a tab 708 disposed at a distal end 122b of the rotatable element 122 with an opening 710 formed therein. The opening 710 can be adapted to receive a tool therethrough, and can be adapted to allow a tool to slide axially while disposed therein, or can be adapted to prevent movement of a tool, e.g., via a frictional fitting, interference fit. Although shown as circular, can have a variety of shapes, including elliptical, square, rectangular, and so on. Alternatively, the tool guide 126 can have a tab 708 with a C-shaped opening or notch, a clip, a fastener secured by a screw or spring, a retaining wire, a hook or hanger, or any other mechanism suitable for receiving a tool. It can be advantageous for the tool guide 126 to removably receive a tool, however, the tool guide 126 can also be fixedly attached to a tool.

As previously mentioned, the endoscopic device 100 can have a control assembly 102 disposed at the proximal end 116a of the elongate shaft 116. The control assembly 102 can have a wide variety of configurations, but in the illustrated embodiment the control assembly 102 includes an optional handle 112 supporting a control, such as a knob 104, and a control spool 110 adapted for receiving the control wire 114. The control assembly 102 can be coupled to the proximal end 116a of the elongate shaft 116 and can be adapted to accommodate or be integrated into an endoscope, the handle of an endoscope, or a working channel associated with an endoscope. In other embodiments, the control assembly 102 can be physically remote to the elongate shaft 116. As will be apparent to those skilled in the art, the handle 112 can be in the form of a pistol grip, wand, or any form suitable for handheld use, such as with a laparoscopic device or a device designed for use without an endoscope. The knob 104 can have gripping indentations 108 formed thereon and can be rotatable around pin 106. The knob 104 can be coupled to the control spool 110 in a wide variety of ways. For example, the knob 104 and the control spool 110 can share pin 106 as a direct and common axle, or alternatively, the knob 104 can be coupled through one or more gears to the control spool 110, which arrangement can be advantageous for reducing the user force necessary to rotate the knob 104 and/or for increasing the degree of precision with which the control spool can be operated. In other embodiments, the knob 104 can drive an input to an control system, e.g., for driving the control spool 110 with an electric motor. In yet further embodiments, the control spool 110 can be omitted and the knob 104 can drive a pinion gear against a pair of racks such that rotation of the knob 104 effects proximal movement of a first rack and a corresponding distal movement of a second rack. Each rack can be connected to an end of the control wire 114. In addition, the control spool 110 or the knob 104 can be spring-biased such that upon release of the knob 104, the control spool 110 can rotate under the force of a spring to return to a rest position, which can rotate the rotatable element 122 accordingly.

As shown in FIG. 1 and mentioned previously, a control wire 114 can couple the control spool 110 to the spool 128 of the rotatable element 122. The control wire can have a variety of configurations, but as shown the control wire 114 is in the form of a loop, one end of the loop wrapped at least partway around control spool 110, the wires of the loop extending through control wire lumens 500, 502 to the spool 128, where the other end of the loop is wrapped at least partway around the spool 128. The control wire 114 need not be a loop but can also be a length of wire attached to the control spool 110 or the spool 128, e.g., a control wire extending through the control wire lumen 500, with one end of the control wire attached to the control spool 110 and the other end attached to the spool 128, so that rotation of the control spool 110 causes rotation of the spool 128, or vice versa. In such a case, a second control wire can extend through a second control wire lumen 502, with one end attached to the control spool 110 and the other end attached to the spool 128. Rotation of the control spool 110 can wind the control wire thereon while unwinding the second control wire, or vice versa, causing the spool 128 to rotate.

The control wire 114 can be made of any material suitable for use within the body, including stainless steel or a titanium alloy, and can be constructed in a variety of ways. As shown, the control wire 114 is a solid wire, however the control wire 114 can also be formed of braided or twisted wires or fibers, chain-links, a ribbon, a belt, and so on. The control wire 114 can also have a coating or surface treatment on at least a portion thereof for aiding in movement, e.g., a bio-compatible lubricant or a resin such as a Teflon® coating. The coating or surface treatment can also aid in gripping the spool, e.g., as with a rubberized coating or with ridges or indentations formed on the wire surface. The properties desired in the control wire 114, including its rigidity, flexibility, malleability, and so on can inform the composition and/or configuration of the control wire 114.

Figure 8:
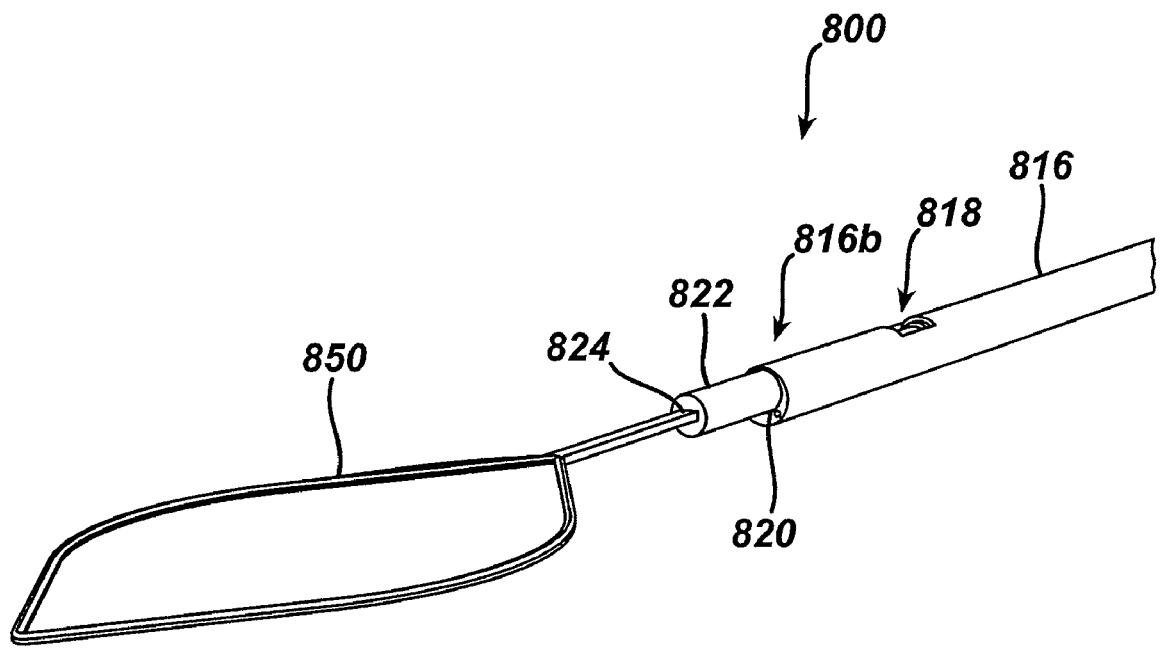
FIG. 8 is a perspective view of alternate embodiment of an endoscopic device having an elongate shaft, a rotatable element, and a snare loop tool disposed therethrough.

As one skilled in the art will understand, the endoscopic device 100 can have a wide variety of other configurations. For example, the endoscopic device 100 can have multiple tool guides 126 and/or multiple lumens 130 for receiving tools. In use, such an arrangement can be effective to cause each tool guide 126 and any tool received therein to orbit a longitudinal axis, such as axis 132, of the rotatable element 122. Alternatively, the endoscopic device 100 can be adapted to accommodate a single tool. For example, FIG. 8 shows an exemplary endoscopic device 800 adapted to receive a snare loop tool 850. As shown, the endoscopic device 800 has an elongate shaft 816 with a lumen 820 formed therein. A rotatable element 822 is partially disposed in the lumen 820 at the distal end 816b of the elongate shaft 816. The rotatable element 822 has a rectangular lumen 824 formed therein. The snare loop tool 850 extends through the rectangular lumen 824, such that rotation of the rotatable element 822 is effective to rotate the snare loop tool 850. As one skilled in the art will readily understand, it is also possible to adapt the endoscopic device 100 shown in FIG. 1 to accommodate a single tool by eliminating the lumen 124 in the rotatable element 122, so that a single tool disposed in the tool guide 126 can be orbited around a longitudinal axis of the rotatable element 122, such as axis 132. In yet further embodiments, the attributes of the rotatable element 122 and the attributes of a separate tool can be combined into one end effector capable of rotation. For example, the rotatable element 122 can have a cutting surface formed thereon and be adapted to cut tissue upon rotation, or can be in the form of a grasper, such as the grasper 306 of FIG. 3, and be adapted to manipulate tissue upon rotation. A wide array of further variations will be apparent to those skilled in the art.

The present invention also provides methods for manipulating tools at a surgical site. In one exemplary method, an endoscopic device, such as the endoscopic device 100 shown in FIG. 1, can be positioned at a surgical site. The endoscopic device 100 can be positioned at a surgical site by inserting the distal end of the endoscopic device 100 through a working channel associated with an endoscope, e.g., a working channel formed in the endoscope itself or coupled to the endoscope. Either before or afterwards, the endoscope can be advanced through a natural orifice such as the mouth and through a body lumen, or through an incision made in the body, to a desired position in the body. The endoscopic device 100 can also be inserted into the body separate from any endoscope. The insertion may be associated with or preceded by any number of procedures to flex, shape, measure, steer, turn, rotate, lubricate and/or guide the endoscopic device 100 in the working channel of the lumen and/or in the body.

Tools can be inserted through the endoscopic device 100, e.g., through the first lumen 120 of the elongate shaft and the lumen 124 of the rotatable element 122, and/or through the second lumen 130 of the elongate shaft 116. A tool inserted through the second lumen 130 can also be coupled to the tool guide 126. A wide variety of tools can be used with the endoscopic device 100. FIG. 3 shows exemplary tools inserted through the endoscopic device 100 of FIG. 1. As shown, a needle-knife 300 can extend through the second lumen 130 and can be received by the tool guide 126. The needle-knife 300, for example, can be an RF needle-knife having an insulating sheath 302 and a conductive wire 304 for transmitting energy into body tissue. A grasper 306 can extend through the first lumen 120 of the elongate shaft 116 and through the lumen 124 of the rotatable element 122. The grasper 306, for example, can include opposing jaws 308, 310 for grasping tissue. The insertion of a tool and coupling of a tool to the tool guide 126 can occur before or after insertion of the endoscopic device 100 into a working channel of an endoscope or into the body.

The rotatable element 122 can be rotated on a longitudinal axis thereof, such as axis 132 shown in FIG. 1. Rotation of the rotatable element 122 can be effected and controlled in a variety of ways, but with the endoscopic device 100 in FIG. 1 a user can turn the knob 104 to rotate the control spool 110 and, by way of the control wire 114 and spool 128, rotate the rotatable element 122. Rotation can also be controlled by manipulation or operation of any kind of control on the control assembly 102, as previously described. In some embodiments, rotation of the rotatable element 122 can be effective to cause the tool guide 126 to orbit a longitudinal axis, such as axis 132, of the rotatable element 122, which can cause the distal end of a tool coupled to the tool guide 126 to orbit the distal end of a tool extending through the lumen 124 of the rotatable element 122. In the context of the example previously discussed with respect to FIG. 3, the grasper 306 can be used to grasp tissue at a surgical site. The RF needle-knife 300 can be orbited around the grasper 306 to perform a resection of the tissue held by the grasper 306. In other embodiments, the rotatable element 122 itself can be a tool, and rotation of the rotatable element 122 can manipulate tissue. In yet further embodiments, rotation of the rotatable element 122 can rotate a tool disposed therethrough. For example, in the context of FIG. 8, rotation of the rotatable element 822 can be effective to manipulate or position the snare loop tool 850 as desired by a user. As one skilled in the art will understand, use of the tools with the endoscopic device 100 can involve other operating or otherwise controlling the tool, e.g., energizing the RF needle-knife 300, manipulating the grasper 306, tightening the snare loop tool 850, and so on.

Rotation of the rotatable element 122 and/or manipulation of any tools can be repeated or continued as desired. In addition, the tools can be moved proximally and/or distally within one or more lumens 120, 130, 124 formed in the endoscopic device 100, e.g., by sliding them. Such proximal and/or distal movement can be advantageous, for example, to adjust the position of tools relative to one another, to adjust the depth of an incision made by an RF needle knife, to allow a grasper to engage body tissue or expose body tissue for resection, to change the diameter of a circular incision made by an RF needle knife, and so on. In some embodiments, the tools need not be removed from the tool guide 126 to be moved proximally and/or distally but can slide within the opening formed therein. Also, the elongate shaft 116 and/or the endoscopic device 100 can be moved proximally and/or distally within a working channel of an endoscope through which the endoscopic device 100 can be disposed. Proximal and/or distal movement can be effected by sliding the elongate shaft 116 within a working channel, and/or by moving the elongate shaft 116 between selectable positions created by surface features such as indentations or notches, as previously described.

Additional aspects of an exemplary method, which will be recognized by one skilled in the art, can include the withdrawal and reintroduction of one or more tools within lumens 120, 124, and 130 of the endoscopic device, the withdrawal and reintroduction of the endoscopic device 100 from a working channel associated with an endoscope or from the surgical site, and the withdrawal of the endoscopic device 100 from the body.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the invention described herein will be processed before surgery. First, a new or used tool is obtained and if necessary cleaned. The tool can then be sterilized. In one sterilization technique, the tool is placed in a closed and sealed container, such as a plastic or TYVEK bag. The container and tool are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An endoscopic device, comprising:
   an elongate shaft having a first lumen and a second lumen formed therein, each of the first and the second lumens adapted to receive a tool therethrough; and
   a rotatable element disposed at a distal end of the elongate shaft, the rotatable element having a lumen formed therein for receiving a tool inserted through the first lumen and a tool guide for receiving a tool inserted through the second lumen;
   a control wire extending through a first control wire lumen and a second control wire lumen, both of which are formed in the elongate shaft, the control wire being and wrapped at least partway around a spool formed on the rotatable element; and
   a control associated with the proximal end of the elongate shaft and coupled to the control wire to effect movement thereof;
   wherein movement of the control wire is effective to rotate the rotatable element on a longitudinal axis thereof such that the tool guide orbits the longitudinal axis of the rotatable element.

2. The device of claim 1, wherein the spool formed on the rotatable element includes an engagement surface for engaging the control wire that is configured to rotate the rotatable element on the longitudinal axis thereof.

3. The device of claim 1, wherein the rotatable element is disposed at least partially within the first lumen of the elongate shaft.

4. The device of claim 1, wherein the tool guide is formed on an exterior surface of the rotatable element.

5. The device of claim 1, wherein the elongate shaft is adapted to be inserted through a working channel associated with an endoscope.

6. The device of claim 1, further comprising a cutting tool adapted to be removeably and replaceably extended through the second lumen of the elongate shaft and received by the tool guide;
   wherein rotation of the rotatable element on the longitudinal axis thereof orbits the distal end of the cutting tool around the longitudinal axis of the rotatable element.

7. An endoscopic system, comprising:
   an elongate shaft having proximal and distal ends and a lumen formed therein for receiving a tool therethrough;
   an end effector disposed at a distal end of the elongate shaft and having a spool formed thereon; and
   a control wire extending through a first control wire lumen and a second control wire lumen, both of which are formed in the elongate shaft;
   the control wire having a proximal portion coupled to a control spool at a proximal end of the elongate shaft and a distal portion wrapped at least partway around the spool of the end effector such that rotation of the control spool moves the control wire so as to rotate the spool of the end effector and thereby rotate the end effector on a longitudinal axis thereof.

8. The system of claim 7, wherein the end effector includes a lumen formed therein and contiguous with the lumen of the elongate shaft.

9. The system of claim 7, wherein the end effector includes a tool guide adapted to receive a tool and formed on an exterior surface of the end effector, and rotation of the end effector is effective to orbit the tool guide around the longitudinal axis of the end effector.

10. The system of claim 7, wherein the end effector is disposed at least partially within the lumen of the elongate shaft.

11. The system of claim 7, further comprising an endoscope having a working channel associated therewith, wherein the elongate shaft is adapted to extend through the working channel.

* * * * *